US009895400B2

(12) United States Patent
Chen et al.

(10) Patent No.: US 9,895,400 B2
(45) Date of Patent: *Feb. 20, 2018

(54) COMPOSITION AND USE OF *LACTOBACILLUS REUTERI* GMNL-263 IN DECREASING BLOOD LIPID LEVELS

(71) Applicant: GENMONT BIOTECH INC., Tainan (TW)

(72) Inventors: Yi-Hsing Chen, Tainan (TW); Ya-Hui Chen, Chiayi County (TW); Tzu-Chi Lou, Taipei (TW); Ting-Yun Shen, Taichung (TW)

(73) Assignee: Genmont Biotech Inc., Tainan (TW)

( * ) Notice: Subject to any disclaimer, the term of this patent is extended or adjusted under 35 U.S.C. 154(b) by 29 days.

This patent is subject to a terminal disclaimer.

(21) Appl. No.: 14/618,188

(22) Filed: Feb. 10, 2015

(65) Prior Publication Data

US 2016/0095889 A1 Apr. 7, 2016

(30) Foreign Application Priority Data

Oct. 2, 2014 (TW) .............................. 103134389 A

(51) Int. Cl.
*C12N 1/20* (2006.01)
*A61K 35/747* (2015.01)
*C12R 1/225* (2006.01)
*A23L 33/135* (2016.01)

(52) U.S. Cl.
CPC .......... *A61K 35/747* (2013.01); *A23L 33/135* (2016.08); *C12N 1/20* (2013.01); *C12R 1/225* (2013.01); *A23V 2002/00* (2013.01); *A23Y 2220/71* (2013.01)

(58) Field of Classification Search
None
See application file for complete search history.

(56) References Cited

U.S. PATENT DOCUMENTS

| 8,298,526 B2 * | 10/2012 | Leu | ........................... C12N 1/20 424/93.1 |
| 2001/0048918 A1 * | 12/2001 | Lievense | .............. A23D 7/0056 424/93.4 |
| 2012/0183504 A1 * | 7/2012 | Lu | ........................ A61K 35/745 424/93.3 |

FOREIGN PATENT DOCUMENTS

| TW | I355939 B1 | 1/2012 |
| TW | I387460 B1 | 3/2013 |
| TW | I440465 B | 6/2014 |
| TW | I441643 B | 6/2014 |

OTHER PUBLICATIONS

Shi et al., British Journal of Nutrition (2013), 109, 263-272, First published online May 1, 2012.*
Taranto et al., J Dairy Sci. Sep. 1998;81(9):2336-40.*
Jones, et al., European Journal of Clinical Nutrition 66, 1234-1241 (Nov. 2012).*

* cited by examiner

*Primary Examiner* — Irene Marx

(57) ABSTRACT

A use of a *Lactobacillus reuteri* GMNL-263 in decreasing blood lipid levels is disclosed. *Lactobacillus reuteri* GMNL-263 (accession No.: CCTCC M 209263) specifically inhibits gene expression related to pro-inflammatory factor and lipid synthesis and promotes gene expression related to cholesterol metabolism. *Lactobacillus reuteri* GMNL-263 is utilized to produce a composition for decreasing blood lipid levels, thereby achieving the aim of hyperlipidemia treatment.

3 Claims, 4 Drawing Sheets

COMPOSITION AND USE OF *LACTOBACILLUS REUTERI* GMNL-263 IN DECREASING BLOOD LIPID LEVELS

BACKGROUND OF THE INVENTION

Field of the Invention

The present invention relates a composition and use of *Lactobacillus reuteri* GMNL-263 in decreasing blood lipid levels. More particularly, a composition comprising *Lactobacillus reuteri* could inhibit the gene expression of tumor necrosis factor alpha (TNF-α), fatty acid synthase (FAS), and sterol regulatory element binding protein-1c (SREBP-1c) and promote the gene expression of LDL receptor and cholesterol 7a-hydroxylase (CYP7A1), achieving the aim of decrease of blood lipid levels.

Description of Related Art

Because of the more and more exquisite food and the increase of the chance of eating at the restaurant, it causes that human intake too much calorie and lipids to accumulate in the body, easily arising hyperlipidemia. According to the research reports, hyperlipidemia easily leads to fatty liver disease and atherosclerosis and is also a key risk factor to cause hypertension, heart disease, stroke, diabetes, arteriosclerosis, kidney disease etc. Therefore, people became deeply concerned that how to keep blood lipid levels normal to reduce the chance of suffering from cardiovascular disease.

At present, the way that natural extracts is the major material to produce composition for reducing blood lipid levels is more and more popular with consumers. For example, the Taiwan Patent application with the Issue No. 1387460, "EXTRACTION METHODS AND COMPOSITIONS TO AMELIORATE HYPERLIPIDEMIA, HYPERGLYCERMIA AND FATTY LIVER", disclosed that extraction methods and compositions of bitter gourd, licorice, soybean protein, and chlorella could exert the highest activation ability of PPAR and further demonstrated the efficacy in animal models and human models to ameliorate hyperlipidemia, hyperglycermia and fatty liver; the Taiwan Patent application with the Issue No. 1441643, "COMPOSITION FOR ADJUSTING BLOOD LIPID AND CARDIOVASCULAR PROTECTION", disclosed a composition for adjusting blood lipids and cardiovascular protection, comprising rhodiola compound powder, Red Yeast Rice, phytosterols, natto and vitamin B complex, wherein the predetermined ratio of the rhodiola compound powder to the Red Yeast Rice and the phytosterols to natto and vitamin B complex represents 54-79 to 14-39 to 7-32 wt %, and the rhodiola compound powder comprises roselle, rhodiola, salvia miltiorrhiza, folium mori, cassia, lotus leaf, hawthorn, chlorella and the composition thereof; the Taiwan Patent application with the Issue No. 1440465, "HERBAL EXTRACT MIXTURE FOR REDUCING BLOOD LIPID AND A COMBINATION THEREOF", disclosed an herbal extract mixture for reducing blood lipid, comprising 33.4% to 77.7% of *Eucheuma okamurai* Yamada extract, 11.14% to 33.3% of *Acanthopanax senticosus* extract, and 11.14% to 33.3% of *Dioscorea alata* extract, and disclosed a combination for reducing blood lipid, including a herbal extract mixture mentioned above and at least a medically acceptable adjuvant or carrier. However, the natural extracts easily have the problem of unknown ingredients or the remains of organic solvents.

Probiotics are microorganisms for beneficial to improve gastrointestinal (GI) tract health of the host (like human or other animals), which are mainly divided into bacteria and yeast. Bacteria are further divided into Lactobacilli and *Bifidobacterium*. At present, some research have reported that probiotics not only modulates immune system and keeps gastrointestinal tract health, but also contributes to cancer prevention. Moreover, please refer to the Taiwan Patent application with the Issue No. 1355939, "COMPOSITION AND USE OF PROBIOTIC STRAIN GM-263 (ADR-1) IN TREATING RENAL FIBROSIS IN DIABETES", disclosed a use of probiotic strain GM-263 (ADR-1) in treating renal fibrosis in diabetes, utilizing the probiotic strain such as *Lactobacillus reuteri* strain GM-263 (ADR-1) (accession No. CCTCC M 209263) to produce a composition for treating renal fibrosis in diabetes in an effective dose, thereby reducing the concentration of glycated hemoglobin and blood sugar and keeping body weight and kidney weight within normal range, as well as specifically inhibiting phosphorylation of JAK2/STAT1 signal transduction pathway and renal fibrosis-related protein expression. It showed that probiotics have beneficial effect of blood sugar regulation and kidney function improvement.

However, according to the above research, probiotics application in reducing blood lipid and the relative mechanism is very few. Therefore, if probiotics could be researched to find beneficial effects for reducing blood lipid and could be produced to medical composition or food material for consumers, it is beneficial to consumers' health.

SUMMARY OF THE INVENTION

Therefore, the object of the present invention is to provide a *Lactobacillus reuteri* GMNL-263 utilizing to produce a composition for decreasing blood lipid levels. *Lactobacillus reuteri* GMNL-263 (GMNL-263) inhibits the gene expression related to pro-inflammatory factor and lipid synthesis and promotes the gene expression related to cholesterol metabolism to decrease blood lipid levels, achieving the aim of hyperlipidemia treatment.

For the above object, a probiotics composition for decreasing blood lipid levels comprises a therapeutically effective amount of *Lactobacillus reuteri* GMNL-263. *Lactobacillus reuteri* GMNL-263 was deposited under the Budapest Treaty to the China Center for Type Culture Collection (CCTCC) at Wuhan University, Wuhan 430072 P.R. China on Nov. 13, 2009 having accession. No.: CCTCC M 209263. *Lactobacillus reuteri* GMNL-263 specifically inhibits gene expression related to pro-inflammatory factor and lipid synthesis and promotes gene expression related to cholesterol metabolism, achieving the aim of decreasing blood lipid levels.

According to an embodiment of the present invention, the gene related to lipid synthesis is fatty acid synthase (FAS) gene and sterol regulatory element binding protein-1c (SREBP-1c) gene. The gene related to cholesterol metabolism is Low-density Lipid receptor (LDLR) gene and cholesterol 7a-hydroxylase (CYP7A1) gene. The pro-inflammatory factor is tumor necrosis factor alpha (TNF-α).

According to an embodiment of the present invention, the probiotics composition is a medical composition, a food additive, a food or its ingredient, and *Lactobacillus reuteri* GMNL-263 is heat-inactivated. The medical composition comprises a pharmaceutically acceptable vehicle and is oral administration.

According to an embodiment of the present invention, the blood lipid levels comprises a serum total cholesterol level, a serum low-density lipoprotein level, a serum malondiaidehyde level, a liver total cholesterol level, and a liver malondiaidehyde level. Furthermore, the *Lactobacillus reu-* teri GMNL-263 modulates the intestinal microbiota. Therefore, the composition comprising *Lactobacillus reuteri* could efficiently regulating blood lipid levels to return to normal range for achieving the aim of hyperlipidemia treatment.

A method for decreasing blood lipid levels is also provided, comprising the step of administrating a therapeutically effective amount of *Lactobacillus reuteri* GMNL-263 (accession No.: CCTCC M 209263) to specifically inhibit gene expression related to pro-inflammatory factor and lipid synthesis and to promote gene expression related to cholesterol metabolism.

DETAILED DESCRIPTION OF THE PREFERRED EMBODIMENT

Figure 1:
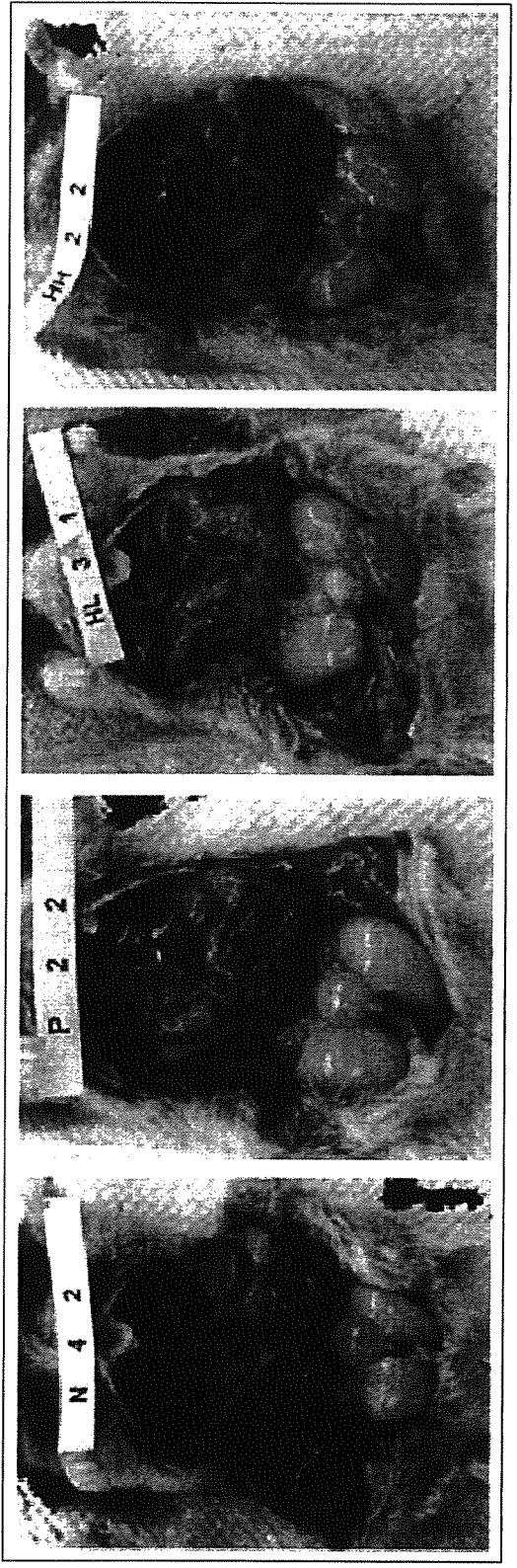
FIG. 1 shows abdominal anatomical photographs of each group of experimental mice according to an embodiment of the present invention.

A probiotics composition for decreasing blood lipid levels is disclosed, comprising a therapeutically effective amount of *Lactobacillus reuteri* GMNL-263 (GMNL-263) (accession No.: CCTCC M 209263). *Lactobacillus reuteri* GMNL-263 specifically inhibits gene expression related to pro-inflammatory factor and lipid synthesis and promotes gene expression related to cholesterol metabolism, achieving the aim of decrease of blood lipid levels. The gene related to lipid synthesis is fatty acid synthase (FAS) gene and sterol regulatory element binding protein-1c (SREBP-1c) gene. The gene related to cholesterol metabolism is Low-density Lipid receptor (LDLR) gene and cholesterol 7a-hydroxylase (CYP7A1) gene. The pro-inflammatory factor is tumor necrosis factor alpha (TNF-α) Therefore, the composition comprising *Lactobacillus reuteri* is suitable for producing a medical composition, a food additive, a food or its ingredient for hyperlipidemia treatment, achieving the aim of decrease of blood lipid levels.

The probiotics composition of the present invention includes, but not be limited to, food, beverage, health food, additive for use in animal feed and drinking water, medical composition for human use and animal use, food additive, and beverage additive.

The term "pharmaceutically acceptable" means that a substance or a composition should be compatible with other ingredients and harmless to patient. The pharmaceutically acceptable vehicle is selected from the group consisting of a solvent, an emulsifier, a suspending agent, a decomposer, a binding agent, an excipient, a stabilizing agent, a chelating agent, a diluent, a gelling agent, a preservative, a lubricant, and a surfactant.

The foregoing *Lactobacillus reuteri* isolated strain and a pharmaceutically acceptable vehicle could be made into a formulation suitable for the probiotics composition of the present invention, according to the technique that those skilled in the art known. The formulation includes, but not be limited to, a solution, an emulsion, a suspension, a powder, a tablet, a pill, a lozenge, a troche, a chewing gum, and a capsule.

The "probiotics" described herein refers to *Lactobacillus reuteri* GMNL-263. *Lactobacillus reuteri* GMNL-263 has been deposited with the China Center for Type Culture Collection (CCTCC), Wuhan University, Wuhan 430072, People's Republic of China under accession number of CCTCC M 209263.

The foregoing probiotics GMNL-263 is obtained by the prior methods and isolated from the gastrointestinal tract of health human volunteers, for example, followed by a microbiological examination, such as 16S rDNA sequence analysis and any commercially available product. The isolated probiotics is identified as *Lactobacillus reuteri* GMNL-263 by the prior method, so the detail identification method is not described here. The effects of the heat-inactivated *Lactobacillus reuteri* GMNL-263 on blood lipid regulation are mainly evaluated as following.

Preparation of the Heat-Inactivated GMNL-263

*Lactobacillus reuteri* GMNL-263 is stored in Genmont Biotech Incorporation, Taiwan. A standard strain of *Lactobacillus reuteri* GMNL-263 stored in a cryogenic vial was cultured in MRS broth at 37±1□ for 18-36 hours. Then, the fermentation broth was concentrated, and the probiotics of the fermentation broth was made inactive by a heating process under high temperature. Finally, the heat-inactivated probiotics was added with a protection agent and was lyophilized to be a heat-inactivated *Lactobacillus reuteri* GMNL-263 powder with a dosage of $2 \times 10^{10}$ cells/g.

First, 6 week-old male Syrian hamsters purchased from National Laboratory Animal Center (Taipei, Taiwan) were maintained in a plastic cage. Ambient temperature was controlled at 23±1° C. with a relative humidity of 60%, in addition, the animals were housed on a reverse 12 hours light/dark cycle and provided with standard laboratory chow and water ad libitum. All animals were normally maintained for 1 week and then were used for a 12-week experiment. Total 32 hamsters were randomly divided into four groups described below, and each group had eight hamsters:

1. Control group, fed standard chow and RO water everyday for 12 weeks;

2. HFD group, fed high-fat diet (HFD) and RO water everyday for 12 weeks;

3. HFD with low dose of the heat-inactivated GMNL-263 group (HFD+GMNL-263(L)), fed with high-fat diet for 4 weeks, and then fed $4 \times 10^9$ cells of the heat-inactivated GMNL-263 everyday for 8 weeks; and 4. HFD with high dose of the heat-inactivated GMNL-263 group (HFD+GMNL-263(H)), fed with high-fat diet for 4 weeks, and then fed $2 \times 10^{10}$ cells of the heat-inactivated GMNL-263 everyday for 8 weeks.

The preparation method of high-fat diet (HFD) was modified from a normal diet for adult mice, which was added with clarified butter and soybean oil, with reference to a high-energy diet from a experiment method for evaluating the function of blood lipid regulation of health food published by Ministry of Health and Welfare, Taiwan. The high-fat diet was stored at 4° C. The ingredients of the normal diet and the high-fat diet are listed as Table 1.

TABLE 1

| Ingredients (g/kg) | Normal diet | HFD |
| --- | --- | --- |
| Casein | 200 | 232 |
| L-Cystine | 3.0 | 3.0 |
| DL-Methionine | — | 3.5 |
| Corn Starch | 397.48 | 137 |
| Maltodextrin | 132 | 150 |

TABLE 1-continued

| Ingredients (g/kg) | Normal diet | HFD |
|---|---|---|
| Sucrose | 100 | 162.58 |
| Cellulose | 50 | 50 |
| Cholesterol | — | 1.9 |
| Mineral Mix (AIN-93) | 35 | 40.60 |
| Calcium phosphate dibasic | — | 4.64 |
| Vitamin Mix (AIN-93) | 10 | 16.24 |
| Choline Bitartrate | 2.5 | 5 |
| tert-butylhydroquinone | 0.014 | 0.04 |
| Soybean oil | 70 | 40 |
| Lard | — | 153.5 |

After 12-weeks experiment, all animals were sacrificed, and tissue samples were collected for various analysis. FIG. 1 shows abdominal anatomical photographs of each group of experimental animal according to an embodiment of the present invention.

Example 1 Biochemical Analysis of Serum, Liver, and Feces

Biochemical analysis of serum including the concentration of triglyceride (TG), total cholesterol (T-CHO), high-density lipoprotein cholesterol (HDL-CHO), and low-density lipoprotein cholesterol (LDL-CHO) was entrusted to National Laboratory Animal Center in Taiwan.

The malondialdehyde (MDA) content of serum was measured by using a commercially available TBARS Assay Kit (Cayman) according to the manufacturer's instruction. Absorbance at 530 nm was measured by using a microplate spectrophotometer, and the MDA concentration of serum was calculated according to the standard curve established by the concentration of the standard MDA sample.

The lipid content of liver tissue and feces was analyzed. 0.1 g of analyzed tissue was homogenized in 1 ml of chloroform-methanol (volume ratio 2:1). The homogenized tissue was filtered, and the filtrate contained the most of lipid of analyzed tissue. After the volume of the filtrate was adjusted to 5 ml by adding chloroform-methanol (volume ratio 2:1), the analysis of triglyceride content and the total cholesterol content of the filtrate was entrusted by Nanguang clinical laboratory (Tainan, Taiwan).

The data was analyzed by one-way analysis of variance (ANOVA) to determine the significant difference between every experimental groups. The symbol * means that the group has significant difference ($p<0.05$) in comparison with the HFD group.

The results are shown as TABLE 2. The changes in lipid content of serum are the indexes of the ability of the heat-inactivated GMNL-263 to regulate blood lipid levels. Comparison with the HFD group, the T-CHO content of serum was significantly decreased by 23%, and the MDA production was also decreased in HFD+GMNL-263(H) group. However, the content of TG, LDL-CHO, HDL-CHO, the ratio of LDL-CHO to HDL-CHO, and the ratio of HDL-CHO to T-CHO were no significant difference between the HFD+GMNL-263(H) group and the HFD group.

The results about the content of TG, T-CHO, and MDA of liver and feces are also shown in TABLE 2. In liver tissue, comparison with the HFD group, the TG content was decreased by 10% and the MDA production was decreased in HFD+GMNL-263(H) group; however, the T-CHO content was no significant difference. In feces sample, comparison with the HFD group, the content of TG and T-CHO was increased by 110% and 93% respectively in the HFD+GMNL-263(H) group.

Therefore, the heat-inactivated GMNL-263 promotes the cholesterol to be excreted in the feces, thereby reducing the cholesterol absorption in an animal to decrease the cholesterol content of body.

TABLE 2

| Item | C ontrol | HFD | HFD + GMNL-263(L) | HFD + GMNL-263(H) |
|---|---|---|---|---|
| Serum | | | | |
| TG (mg/dl) | 130 ± 8* | 351 ± 66 | 382 ± 107 | 305 ± 75 |
| T-CHO (mg/dl) | 127 ± 8* | 287 ± 37 | 243 ± 61 | 222 ± 26* |
| LDL- CHO (mg/dl) | 18 ± 3* | 86 ± 42 | 91 ± 53 | 65 ± 32 |
| HDL- CHO (mg/dl) | 87 ± 7* | 140 ± 7 | 125 ± 13* | 128 ± 8 |
| LDL- CHO/HDL- CHO | 0.20 ± 0.04* | 0.64 ± 0.36 | 0.69 ± 0.37 | 0.49 ± 0.23 |
| HDL- CHO/T-CHO | 68.58 ± 1.88* | 55.11 ± 4.15 | 48.56 ± 10.74 | 54.00 ± 2.43 |
| MDA (µg/ml) | 4.42 ± 0.63* | 6.30 ± 0.84 | 5.72 ± 0.99 | 4.99 ± 0.15 |
| Liver | | | | |
| TG (mg/dl) | 85.0 ± 6.5* | 93.3 ± 5.3 | 90.7 ± 3.4 | 84.0 ± 4.3* |
| T-CHO (mg/dl) | 89.7 ± 0.5* | 130.0 ± 4.9 | 118.3 ± 12.8 | 127.3 ± 6.0 |
| MDA (µg/ml) | 4.37 ± 0.49* | 8.58 ± 0.68 | 6.95 ± 1.32* | 5.53 ± 0.40* |
| feces | | | | |
| TG (mg/dl) | 5.8 ± 0.8 | 5.0 ± 1.7 | 7.5 ± 1.1 | 10.5 ± 2.0* |
| T-CHO (mg/dl) | 6.7 ± 0.8 | 5.6 ± 1.6 | 8.0 ± 1.7* | 10.8 ± 0.8* |

Example 2 Analysis mRNA Expression Affected by the Heat-Inactivated GMNL-263 in Liver Tissue and Adipose Tissue The mRNA expression in (I) liver tissue and (II) adipose tissue was detected by RT-PCR. The detected genes are described as following:

1. the gene related to proinflammatory factor: interleukin-6 (IL-6) gene and tumor necrosis factor alpha (TNF-α) gene, the expression of which induces the inflammation;

2. the gene related to lipid synthesis: fatty acid synthase (FAS) gene, sterol regulatory element binding protein-1 (SREBP-1c) gene, and peroxisome prolifera proliferator-activated receptor g (PPARγ) gene, wherein the gene expression of FAS and SREBP-1c are related to lipid synthesis, and the gene expression of PPARγ is related to fatty acid metabolism;

3. the gene related to cholesterol metabolism: 3-Hydroxy-3-methylglutaryl-coenzyme A reductase (HMG-CoA R)

gene, LDL-cholesterol receptor (LDLR) gene, and cholesterol 7a-hydroxylase (CYP7A1) gene, wherein the gene expression of HMG-CoA R is related to cholesterol synthesis, and the gene expression of LDLR and CYP7A1 are related to cholesterol metabolism.

The data was analyzed by one-way analysis of variance (ANOVA) to determine the significant difference between every experimental groups. The symbol * means that the group has significant difference (p<0.05) in comparison with the HFD group.

(I) mRNA Expression Affected by Heat-Inactivated GMNL-263 in Liver Tissue

Figure 2:
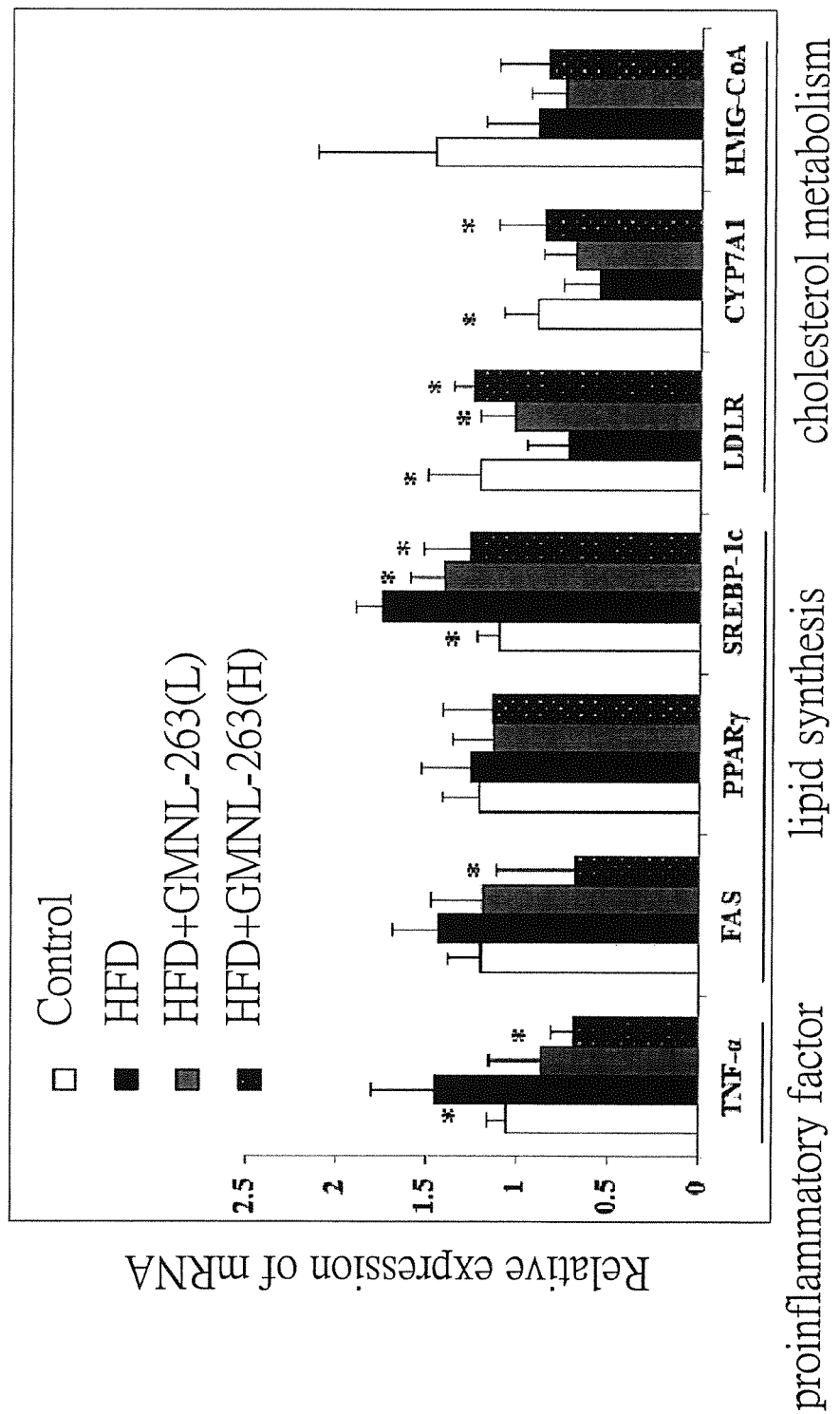
FIG. 2 shows a bar diagram of the relative expression of several mRNA in liver tissue of each group of FIG. 1.

FIG. 2 shows a bar diagram of the relative expression of several mRNA in liver tissue of each group of FIG. 1. About the gene related to proinflammatory factor, the TNF-α gene expression was inhibited in the mice that were fed with high dose of heat-inactivated GMNL-263 ((HFD+GMNL-263 (H) group). About the gene related to lipid synthesis, the gene expression of FAS and SREBP-1 were inhibited in the HFD+GMNL-263(H) group, but there was no significant difference in the PPARγ gene expression. About the gene related to cholesterol metabolism, the gene expression of CYP7A1 and LDLR were promoted in the HFD+GMNL-263(H) group, but the HMG-CoA R gene expression in the same group has no significant change compared with the HFD group.

(II) mRNA Expression Affected by Heat-Inactivated GMNL-263 in Adipose Tissue

Figure 3:
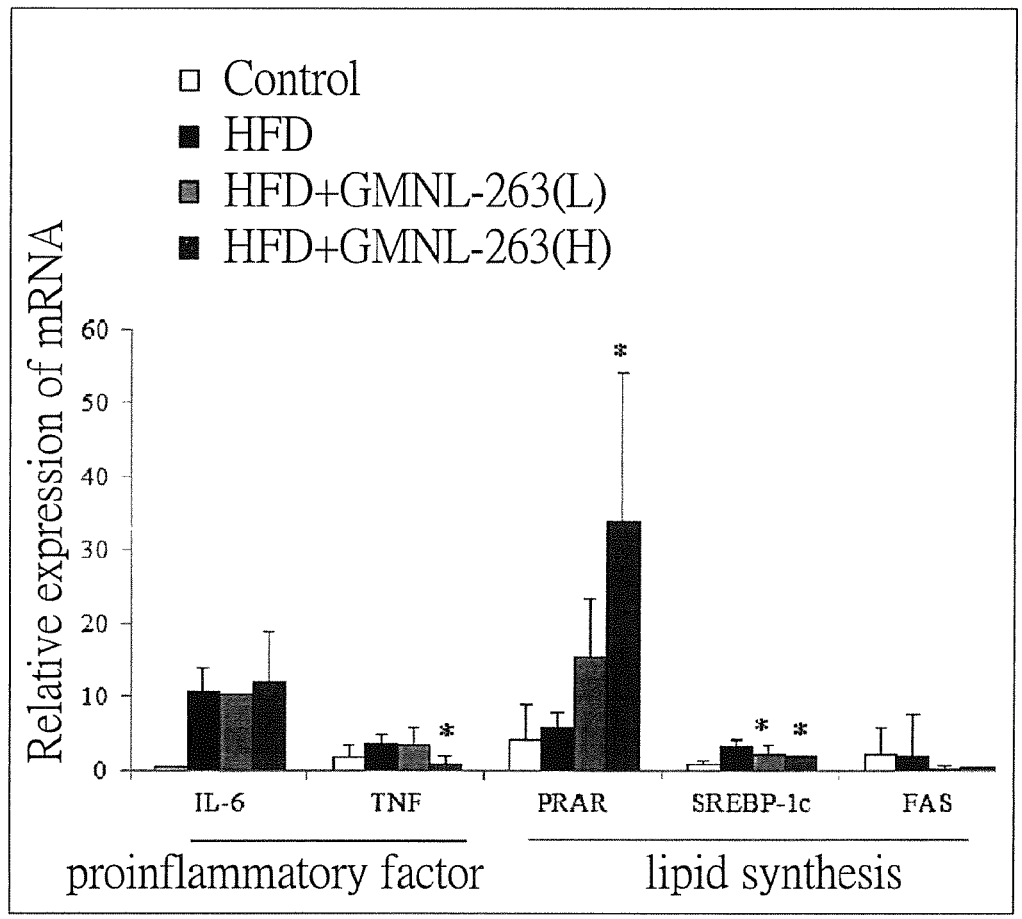
FIG. 3 shows a bar diagram of the relative expression of several mRNA in adipose tissue of each group of FIG. 1.

About the mRNA expression in adipose tissue, the change of gene expression which is related to proinflammatory factor lipid synthesis was observed. FIG. 3 shows a bar diagram of the relative expression of several mRNA in adipose tissue of each group of FIG. 1. The gene expression of TNF-α and SREBP-1c were inhibited in the HFD+GMNL-263(H) group, and the gene of PPARγ was activated in the HFD+GMNL-263(H) group.

According to the results of the foregoing experiment, the heat-inactivated GMNL-263 inhibits the proinflammatory gene expression in liver tissue and adipose tissue and decreases the production of lipid peroxide in the body. It means that the heat-inactivated GMNL-263 has anti-inflammatory and anti-oxidation effects, thereby regulating blood lipid levels. Moreover, the results of gene expression showed that the heat-inactivated GMNL-263 inhibits fatty acid synthesis in liver tissue and promote fatty acid and cholesterol metabolism, and the similar situation was shown in adipose tissue. Therefore, the heat-inactivated GMNL-263 decreases the accumulation of fatty acid and cholesterol in the body.

Example 3 Analysis the Changes in the Intestinal Microbiota Affected by the Heat-Inactivated GMNL-263

Whether the intestinal microbiota affected by the heat-inactivated GMNL-263 has changes was determined by RT-PCR. The content of *Bifidobacterium* and *Clostridium* in the feces was detected.

The data was analyzed by one-way analysis of variance (ANOVA) to determine the significant difference between every experimental groups. The symbol * means that the group has significant difference (p<0.05) in comparison with the HFD group.

Figure 4:
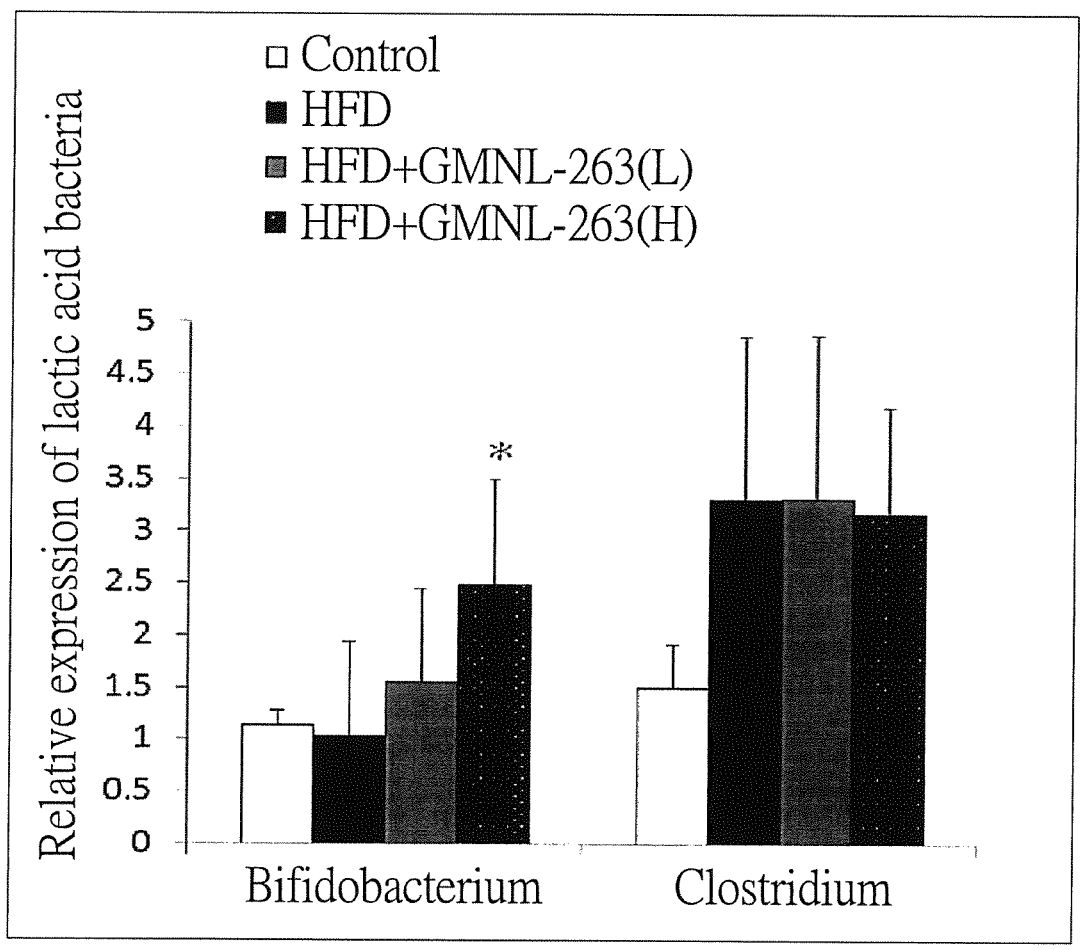
FIG. 4 shows a bar diagram of the relative expression of intestinal microbiota of each group of FIG. 1.

The results are shown in FIG. 4, showing a bar diagram of the relative expression of intestinal microbiota of each group of FIG. 1. Comparison with the HFD group, the content of *Clostridium* was not significantly decreased in the HFD+GMNL-263(H) group, but the content of *Bifidobacterium* was significantly changed in the HFD+GMNL-263 (H) group.

According to the above description and embodiments, the composition and use of *Lactobacillus reuteri* GMNL-263 in decreasing blood lipid levels of the present invention have the advantages as following:

1. *Lactobacillus reuteri* GMNL-263 could be used to decrease the blood lipid levels. *Lactobacillus reuteri* GMNL-263 specifically inhibits the gene expression related to lipid synthesis and promote the gene expression related to cholesterol metabolism, thereby promoting the cholesterol to be excreted and reducing the cholesterol absorption in an animal to decrease the cholesterol content of body, achieving the aim of decreasing the blood lipid levels.

2. *Lactobacillus reuteri* GMNL-263 inhibits the gene expression of proinflammatory factor in the liver tissue and adipose tissue and decreases the production of lipid peroxide in the body. It means that the heat-inactivated GMNL-263 has anti-inflammatory and anti-oxidation effects.

3. Comparison with the Chinese herbal medicine containing complex composition, *Lactobacillus reuteri* GMNL-263 of the present invention could not only keep the intestinal health, but also regulate blood lipid levels. Therefore, *Lactobacillus reuteri* GMNL-263 could further be form a composition for decreasing blood lipid levels, thereby providing a better choice to the consumers.

What is claimed is:

1. A method for decreasing blood lipid levels, liver triglyceride levels and liver malondialdehyde levels of a high fat diet mouse comprising:
   (a) administering an effective amount of 2×10$^{10}$ cells/g heat-inactivated *Lactobacillus reuteri* GMNL-263 probiotic bacteria with the deposition number CCTCC M 209263 to a high fat diet mouse every day for 8 weeks;
   (b) reducing said blood lipid levels, said liver triglyceride levels and said liver malondialdehyde levels by inhibiting gene expression related to pro-inflammatory factor and lipid synthesis and promoting gene expression related to cholesterol metabolism, wherein the gene related to pro-inflammatory factor is tumor necrosis factor alpha, the gene related to lipid synthesis is fatty acid synthase and sterol regulatory element binding protein-1, and the gene related to cholesterol metabolism is LDL receptor and cholesterol 7a-hydroxylase.

2. The method according to claim 1, wherein the blood lipid levels comprise a serum total cholesterol level and a serum low-density lipoprotein level.

3. The method according to claim 1, wherein the *Lactobacillus reuteri* GMNL-263 increases *Bifidobacterium* in the intestinal microbiota.

* * * * *